United States Patent
Miao et al.

(10) Patent No.: US 10,682,344 B2
(45) Date of Patent: Jun. 16, 2020

(54) METHOD OF TREATING LIVER FIBROSIS

(71) Applicant: ChemoCentryx, Inc., Mountain View, CA (US)

(72) Inventors: Zhenhua Miao, San Jose, CA (US); Israel Charo, Mountain View, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 181 days.

(21) Appl. No.: 15/612,124

(22) Filed: Jun. 2, 2017

(65) Prior Publication Data

US 2017/0348293 A1    Dec. 7, 2017

Related U.S. Application Data

(60) Provisional application No. 62/345,086, filed on Jun. 3, 2016.

(51) Int. Cl.
| | | |
|---|---|---|
| *A61K 31/444* | (2006.01) | |
| *A61K 9/08* | (2006.01) | |
| *A61K 45/06* | (2006.01) | |
| *A61K 47/38* | (2006.01) | |
| *A61P 1/16* | (2006.01) | |
| *A61K 9/00* | (2006.01) | |

(52) U.S. Cl.
CPC .......... *A61K 31/444* (2013.01); *A61K 9/0019* (2013.01); *A61K 9/0053* (2013.01); *A61K 9/08* (2013.01); *A61K 45/06* (2013.01); *A61K 47/38* (2013.01); *A61P 1/16* (2018.01)

(58) Field of Classification Search
CPC .. A61K 31/444; A61K 9/0019; A61K 9/0053; A61K 9/08; A61K 45/06; A61K 47/38; A61P 1/16
USPC ........................................................ 514/277
See application file for complete search history.

(56) References Cited

U.S. PATENT DOCUMENTS

| | | | |
|---|---|---|---|
| 8,519,135 B2 * | 8/2013 | Chen ..................... | C07C 311/21 546/113 |
| 2007/0219245 A1 | 9/2007 | Hou et al. | |
| 2009/0197884 A1 | 8/2009 | Ghosh et al. | |
| 2011/0274696 A1 | 11/2011 | Gladue et al. | |
| 2014/0235661 A1 | 8/2014 | Ebel et al. | |
| 2017/0319548 A1 * | 11/2017 | Lefebvre ................ | A61K 45/06 |

FOREIGN PATENT DOCUMENTS

WO    WO 2008/008431 A2    1/2008

OTHER PUBLICATIONS

International Search Report and Written Opinion for related International Application No. PCT/US2017/035628, dated Aug. 29, 2017 (7 pages).

* cited by examiner

*Primary Examiner* — Yevgeny Valenrod

(74) *Attorney, Agent, or Firm* — Barnes & Thornburg LLP; Ryan L. Marshall; Jonathan Hartley

(57) ABSTRACT

A method of treating liver fibrosis with CCR2 antagonists is provided. The liver fibrosis may be associated with non-alcoholic steatohepatitis (NASH), non-alcoholic fatty liver disease (NAFLD), emerging cirrhosis, non-cirrhotic hepatic fibrosis, type 2 diabetes mellitus (T2DM) or metabolic syndrome (MS).

20 Claims, 3 Drawing Sheets

Figure 1: Change in body weight in HFD/fructose-induced NASH model
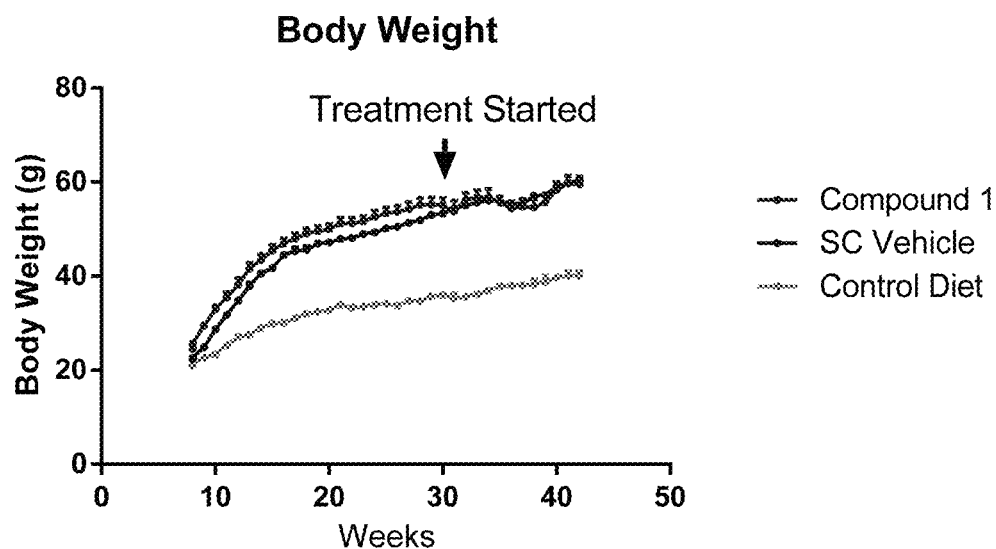
Figure 2: Serum ALT and AST Levels in the HFD/fructose-induced NASH model
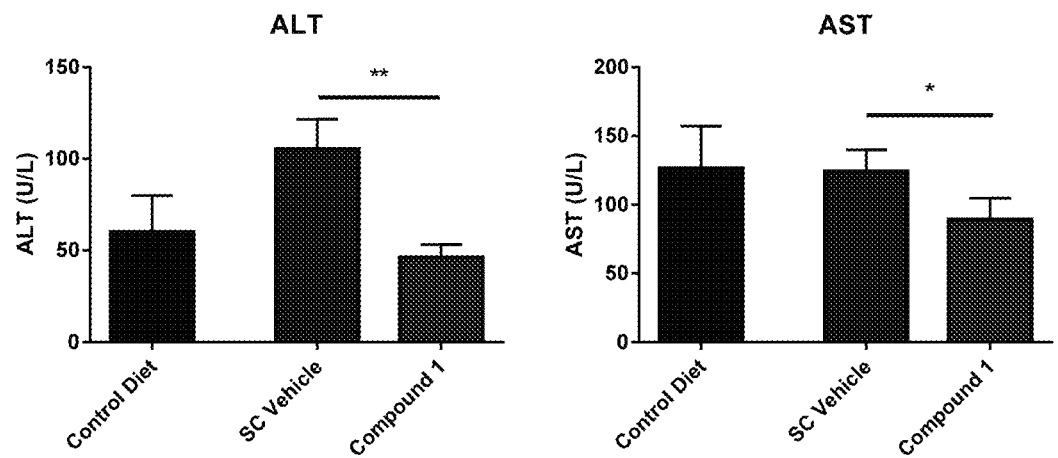

Figure 3: Representative images of Sirius red-stained liver sections of animals treated with vehicle or Compound 1 in HFD/fructose-induced NASH model.
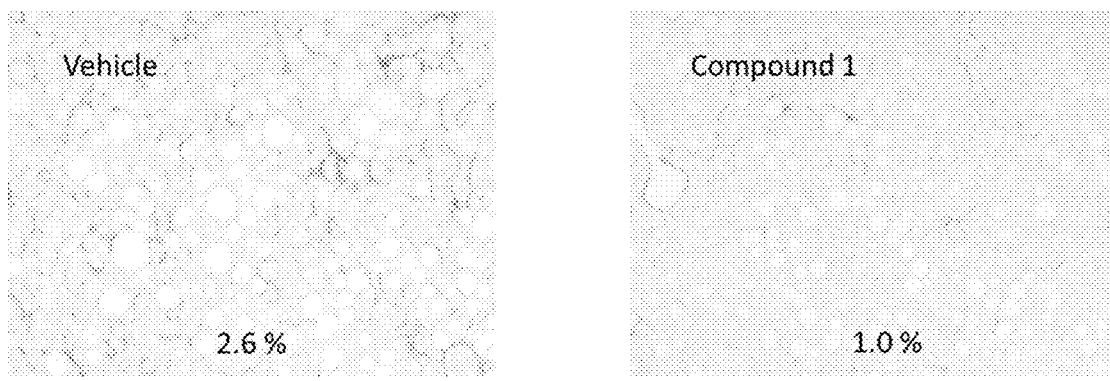
Figure 4: Percentage of Sirius Red staining in animals treated with compound 1 or vehicle in HFD/fructose-induced NASH model
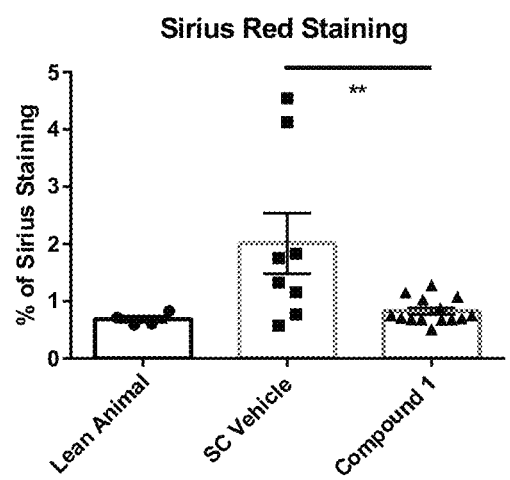

Figure 5: Serum ALT and AST Levels in MCD-induced NASH model
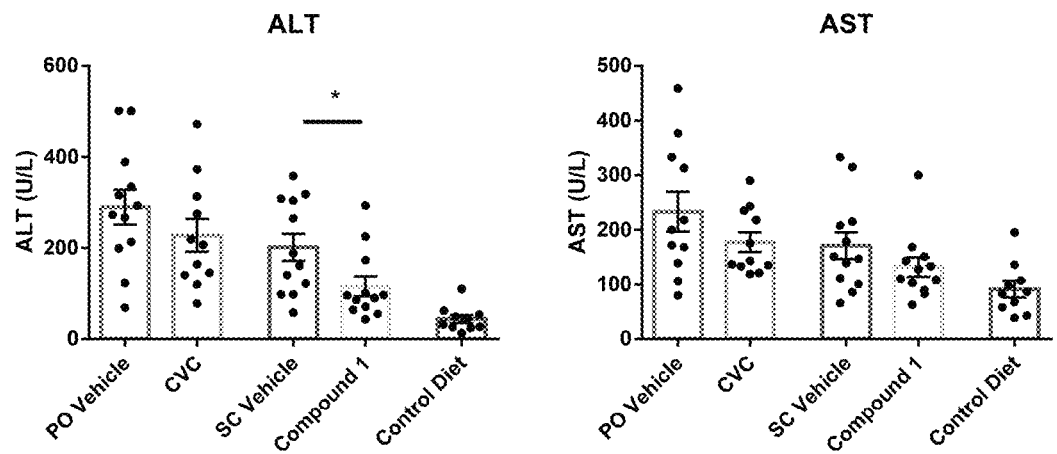
Figure 6: Percentage of Sirius Red Positive area in animals treated with compound 1, CVC or vehicle in MCD-induced NASH model
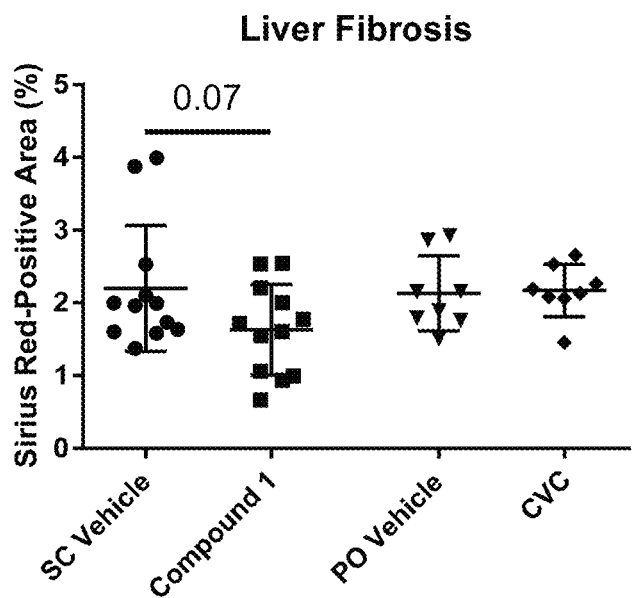

METHOD OF TREATING LIVER FIBROSIS

FIELD

This application claims the benefit under 35 U.S.C. § 119(e) of U.S. Provisional Patent Application No. 62/345,086, filed Jun. 3, 2016, and titled "METHOD OF TREATING LIVER FIBROSIS," which is incorporated, in its entirety, by this reference.

The present disclosure describes methods of treating liver fibrosis with CCR2 antagonists. The liver fibrosis may be associated with non-alcoholic steatohepatitis (NASH), non-alcoholic fatty liver disease (NAFLD), emerging cirrhosis, non-cirrhotic hepatic fibrosis, type 2 diabetes mellitus (T2DM) or metabolic syndrome (MS).

BACKGROUND

Liver fibrosis arises from the excessive accumulation of extracellular matrix proteins including collagen that occurs in most types of chronic liver diseases. Non-alcoholic fatty liver disease (NAFLD) is a medical condition that is characterized by the buildup of fat (called fatty infiltration) in the liver. Up to 85% of patients with NAFLD have diabetes or impaired glucose tolerance. Nonalcoholic steatohepatitis (NASH) is the most severe form of NAFLD in which there is fatty infiltration along with liver inflammation (steatohepatitis). NASH affects 2 to 5 percent of Americans.

Both NASH and NAFLD are becoming more common, possibly because of the increased rate of obesity. Obesity also contributes to diabetes and high blood cholesterol, which can further complicate the health of someone with NASH. Better treatments for liver fibrosis which may be associated with non-alcoholic steatohepatitis (NASH), non-alcoholic fatty liver disease (NAFLD), emerging cirrhosis, non-cirrhotic hepatic fibrosis, type 2 diabetes mellitus (T2DM) or metabolic syndrome (MS) are currently needed.

CCR2 antagonists have been described in U.S. Pat. Nos. 8,519,135, 7,622,583, 7,884,110, and 8,093,247 and U.S. Patent Publication 2006/0173019.

BRIEF SUMMARY

The present disclosure is directed to methods of treating liver fibrosis in a patient comprising administering to the patient in need thereof an effective amount of a compound of Formula I:

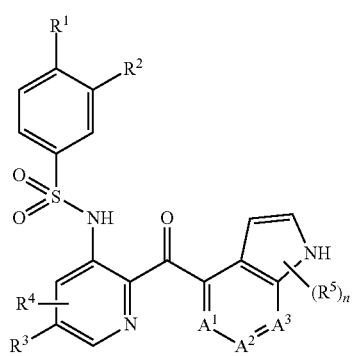

Formula I or a pharmaceutically acceptable salt thereof, wherein
$R^1$ is halogen or $C_{1-6}$ alkyl;
$R^2$ is hydrogen, halogen, $C_{1-6}$ alkyl, $C_{1-6}$ alkoxy, $C_{1-6}$ haloalkyl, $C_{1-6}$ haloalkoxy, or —CN;
$R^3$ is hydrogen, halogen, or $C_{1-6}$ alkyl;
$R^4$ is hydrogen, halogen, or $C_{1-6}$ alkyl;
each $R^5$ is independently $C_{1-6}$ alkyl, —OH, or —$NH_2$;
n is 0, 1, 2, or 3; and
each of $A^1$, $A^2$, and $A^3$ is —CH— or —N—, where at least one of $A^1$, $A^2$, or $A^3$ is —N—.

FIGURES

FIG. 1 illustrates the change in body weight in the HFD/fructose-induced NASH model.

FIG. 2 shows the serum ALT and AST levels in the HFD/fructose-induced NASH model.

FIG. 3 shows representative images of Sirius, red-stained liver sections of animals treated with vehicle or Compound 1 in the FHD/fructose-induced NASH model.

FIG. 4 shows the percentage of Sirius red staining in animals treated with compound 1 or vehicle in the HFD/fructose-induced NASH model.

FIG. 5 shows the serum ALT and AST levels in the MCD-induced NASH model.

FIG. 6 shows the percentage of Sirius red positive area in animals treated with compound 1, CVC or vehicle in the MCD-induced NASH model.

DETAILED DESCRIPTION

Abbreviations and Definitions

When describing the compounds, compositions, methods and processes of this disclosure, the following terms have the following meanings, unless otherwise indicated.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups are unsubstituted, unless otherwise indicated. Examples of substituted alkyl include haloalkyl, thioalkyl, aminoalkyl, and the like.

"Alkoxy" refers to —O-alkyl. Examples of an alkoxy group include methoxy, ethoxy, n-propoxy etc.

"Alkenyl" refers to an unsaturated hydrocarbon group which may be linear, cyclic or branched or a combination thereof. Alkenyl groups with 2-8 carbon atoms are preferred, although alkenyl can have more than 8 carbon atoms. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups are unsubstituted, unless otherwise indicated.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups are unsubstituted, unless otherwise indicated.

"Aryl" refers to a polyunsaturated, aromatic hydrocarbon group having a single ring (monocyclic) or multiple rings (bicyclic), which can be fused together or linked covalently.

Aryl groups with 6-10 carbon atoms are preferred, where this number of carbon atoms can be designated by $C_{6-10}$, for example. Examples of aryl groups include phenyl and naphthalene-1-yl, naphthalene-2-yl, biphenyl and the like. Aryl groups are unsubstituted, unless otherwise indicated.

"Halo" or "halogen", by itself or as part of a substituent refers to a chlorine, bromine, iodine, or fluorine atom.

"Haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic ring containing at least one heteroatom (typically 1 to 5 heteroatoms) selected from nitrogen, oxygen or sulfur. The heterocyclyl ring may be monocyclic or bicyclic. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

In one preferred embodiment, heterocyclic groups may be represented by formula (AA) below:

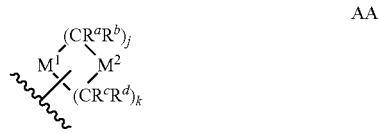

AA where formula (AA) is attached via a free valence on either $M^1$ or $M^2$; $M^1$ represents O, $NR^e$, or $S(O)_i$; $M^2$ represents $CR^fR^g$, O, $S(O)_j$, or $NR^e$; l is 0, 1 or 2; j is 1, 2 or 3 and k is 1, 2 or 3, with the proviso that j+k is 3, 4, or 5; and $R^a$, $R^b$, $R_c$, $R^d$, $R^e$, $R^f$, and $R^g$ are independently selected from the group consisting of hydrogen, halogen, unsubstituted or substituted $C_{1-8}$ alkyl, unsubstituted or substituted $C_{2-8}$ alkenyl, unsubstituted or substituted $C_{2-8}$ alkynyl, —$COR^h$, —$CO_2R^h$, —$CONR^hR^i$, —$NR^hCOR^i$, —$SO_2R^h$, —$SO_2NR^hR^i$, —$NSO_2R^hR^i$—$NR^hR^i$, —$OR^h$, -$Q^1COR^h$, -$Q^1CO_2R^h$, -$Q^1CONR^hR^i$, -$Q^1NR^hCOR^i$, -$Q^1SO_2R^{28}$, -$Q^1SO_2NR^hR^i$, -$Q^1NSO_2R^hR^i$, -$Q^1NR^hR^i$, -$Q^1OR^h$, wherein $Q^1$ is a member selected from the group consisting of $C_{1-4}$ alkylene, $C_{2-4}$ alkenylene and $C_{2-4}$ alkynylene, and $R^h$ and $R^i$ are independently selected from the group consisting of hydrogen and $C_{1-8}$ alkyl, and wherein the aliphatic portions of each of the $R^a$, $R^b$, $R^c$, $R^d$, $R^e$, $R^f$, $R^g$, $R^h$ and $R^i$ substituents are optionally substituted with from one to three members selected from the group consisting of: halogen, —OH, —$OR''$, —OC(O)NHR'', —OC(O)NR''R°, —SH, —SR'', —S(O)R'', —$S(O)_2R''$, —$SO_2NH_2$, —$S(O)_2NHR''$, —$S(O)_2NR''R°$, —$NHS(O)_2R''$, —NR''S(O)$_2R°$, —C(O)NH$_2$, —C(O)NHR'', —C(O)NR''R°, —C(O)R'', —NHC(O)R°, —NR''C(O)R°, —NHC(O)NH$^2$, —NR''C(O)NH$_2$, —NR''C(O)NHR°, —NHC(O)NHR'', —NR''C(O)NR°R$^p$, —NHC(O)NR''R°, —CO$_2$H, —$CO_2R''$, —NHCO$_2R''$, —NR''CO$_2R°$, —CN, —NO$_2$, —NH$_2$, —NHR'', —NR''R°, —NR''S(O)NH$_2$ and —NR''S(O)$_2$NHR°, wherein R'', R° and $R^p$ are independently an unsubstituted $C_{1-8}$ alkyl. Additionally, any two of $R^a$, $R^b$, $R^c$, $R^d$, $R^e$, $R^f$ and $R^g$ may be combined to form a bridged or spirocyclic ring system.

In one preferred embodiment, the number of $R^a+R^b+R^c+R^d$ groups that are other than hydrogen is 0, 1 or 2. In a more preferred embodiment, $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, —CORK, —$CO_2R^h$, —$CONR^hR^h$, —$NR^hCOR^h$, —$SO_2R^h$, —$SO_2NR^hR^i$, —$NSO_2R^hR^i$, —$NR^hR^i$, and —$OR^h$, wherein $R^h$ and $R^i$ are independently selected from the group consisting of hydrogen and unsubstituted $C_{1-8}$ alkyl and wherein the aliphatic portions of each of the $R^a$, $R^b$, $R^c$, $R^d$, $R^e$, $R^f$ and $R^g$ substituents are optionally substituted with from one to three members selected from the group consisting of halogen, —OH, —OR'', —OC(O)NHR'', —C(O)NR''R°, —SH, —SR'', —S(O)R°, —$S(O)_2R''$, —$SO_2NH_2$, —$S(O)_2NHR''$, —$S(O)_2NR''R°$, —NHS(O)$_2R''$, —NR''S(O)$_2R°$, —C(O)NH$_2$, C(O)NHR'', —C(O)NR''R°, —C(O)R'', —NHC(O)R'', —NR''C(O)R°, —NHC(O)NH$_2$, —NR''C(O)NH$_2$, —NR''C(O)NHR°, —NHC(O)NHR'', —NR''C(O)NR°R$^p$, —NHC(O)NR''R°, —CO$_2$H, —$CO_2R''$, —NHCO$_2R''$, —NR$_n$CO$_2R°$, —CN, —NO$_2$, —NH$_2$, —NHR'', —NR''R°, —NR''S(O)NH$_2$ and —NR''S(O)$_2$NHR°, wherein R'', R° and $R^p$ are independently an unsubstituted $C_{1-8}$ alkyl.

In a more preferred embodiment, $R^a$, $R^b$, $R^c$, $R^d$, $R^e$, $R^f$, and $R^g$ are independently hydrogen or $C_{1-4}$ alkyl. In another preferred embodiment, at least three of $R^a$, $R^b$, $R^c$, $R^d$, $R^c$, $R^f$, and $R^g$ are hydrogen.

"Heteroaryl" refers to an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, azaindolyl, azaindazolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups are unsubstituted, unless otherwise indicated. For substituted groups, the substitution may be on a carbon or heteroatom. For example, when the substitution is oxo (=O or —O$^-$), the resulting group may have either a carbonyl (—C(O)—) or a N-oxide (—N$^+$—O$^-$).

Suitable substituents for substituted alkyl, substituted alkenyl, and substituted alkynyl include halogen, —CN, —CO$_2$R', —C(O)R', —C(O)NR'R", oxo (=O or —O$^-$), —OR', —OC(O)R', —OC(O)NR'R"—NO$_2$, —NR'C(O)R", —NR'''C(O)NR'R", —NR'R", —NR'CO$_2$R", —NR'S(O)R", —NR'S(O)$_2$R''', —NR'''S(O)NR'R", —NR'''S(O)$_2$NR'R", —SR', —S(O)R', —S(O)$_2$R', —S(O)$_2$NR'R", —NR'—C(NHR")=NR''', —SiR'R"R''', —N$_3$, substituted or unsubstituted C$_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical.

Suitable substituents for substituted aryl, substituted heteroaryl and substituted heterocyclyl include halogen, —CN, —CO$_2$R', —C(O)R', —C(O)NR'R", oxo (=O or —O$^-$), —OR', —OC(O)R', —OC(O)NR'R", —NO$_2$, —NR'C(O)R", —NR'''C(O)NR'R", —NR'R", —NR'CO$_2$R", —NR'S(O)R", —NR'S(O)$_2$R", —NR'''S(O)NR'R", —NR'''S(O)$_2$NR'R", —SR', —S(O)R', —S(O)$_2$R', —S(O)$_2$NR'R", —NR'—C(NHR")=NR''', —SiR'R"R''', —N$_3$, substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10-membered heterocyclyl. The number of possible substituents range from zero to the total number of open valences on the aromatic ring system.

As used above, R', R" and R''' each independently refer to a variety of groups including hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl). Furthermore, R' and R", R" and R''', or R' and R''' may together with the atom(s) to which they are attached, form a substituted or unsubstituted 5-, 6-, or 7-membered ring.

Two of the substituents on adjacent atoms of an aryl or heteroaryl ring may optionally be replaced with a substituent of the formula -T-C(O)—(CH$_2$)$_q$—U—, wherein T and U are independently —NR""—, —O—, —CH$_2$— or a single bond, and q is an integer of from 0 to 2. Alternatively, two of the substituents on adjacent atoms of the aryl or heteroaryl ring may optionally be replaced with a substituent of the formula -A'-(CH$_2$)$_r$—B'—, wherein A' and B' are independently —CH$_2$—, —O—, —NR""—, —S—, —S(O)—, —S(O)$_2$—, —S(O)$_2$NR""— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR""—, —S—, —S(O)—, —S(O)$_2$—, or —S(O)$_2$NR'—. R"" in is selected from hydrogen or unsubstituted C$_{1-8}$ alkyl.

"Heteroatom" is meant to include oxygen (O), nitrogen (N), sulfur (S) and silicon (Si).

"Above natural isotopic abundance" refers to the abundance of isotopes of a chemical element as naturally measured.

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M. et al, "Pharmaceutical Salts", J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

"Therapeutically effective amount" refers to an amount sufficient to effect treatment when administered to a patient in need of treatment.

"Treating" or "treatment" as used herein refers to the treating or treatment of a disease or medical condition in a patient, such as a mammal (particularly a human or a companion animal) which includes ameliorating the disease or medical condition, i.e., eliminating or causing regression of the disease or medical condition in a patient; suppressing the disease or medical condition, for example slowing or arresting the development of the disease or medical condition in a patient; or alleviating the symptoms of the disease or medical condition in a patient; or preventing the disease to develop.

Certain compounds of the present disclosure can exist in unsolvated forms as well as solvated forms, including hydrated forms. In general, both solvated forms and unsolvated forms are intended to be encompassed within the scope of the present disclosure.

It will be apparent to one skilled in the art that certain compounds of the present disclosure may exist in tautomeric forms, all such tautomeric forms of the compounds being within the scope of the disclosure. Certain compounds of the present disclosure possess asymmetric carbon atoms (optical centers) or double bonds; the racemates, diastereomers, geometric isomers and individual isomers (for example separate enantiomers) are all intended to be encompassed within the scope of the present disclosure.

The compounds may be prepared such that any number of hydrogen atoms are replaced with a deuterium ($^2$H) isotope. The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. All isotopic variations of the compounds of the present disclosure, whether radioactive or not, are intended to be encompassed within the scope of the present disclosure. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment.

Method of Treating Liver Fibrosis

The present disclosure provides methods of treating liver fibrosis in a patient comprising administering to the patient in need thereof an effective amount of a compound of Formula Ia:

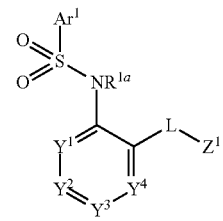

(Ia)

or a pharmaceutically acceptable salt thereof, wherein
$Ar^1$ is selected from the group consisting of substituted or unsubstituted $C_{6-10}$ aryl and substituted or unsubstituted 5- to 10-membered heteroaryl;

$R^{1a}$ is selected from the group consisting of hydrogen, substituted or unsubstituted $C_{1-8}$ alkyl, substituted or unsubstituted $C_{2-6}$ alkenyl, substituted or unsubstituted $C_{2-6}$ alkynyl, and substituted or unsubstituted 3- to 10-membered heterocyclyl;

$Y^1$ is selected from the group consisting of —$CR^{2a}$—, —N—, and —$N^+(O)^-$—;

$Y^2$ is selected from the group consisting of —$CR^{2b}$—, —N—, and —$N^+(O)^-$—;

$Y^3$ is selected from the group consisting of —$CR^{2c}$—, —N—, and —$N^+(O)^-$—;

$R^{2a}$, $R^{2b}$, and $R^{2c}$ are each independently selected from the group consisting of hydrogen, halogen, —CN, —C(O)$R^{3a}$, —CO$_2R^{3a}$, —C(O)$NR^{3a}R^{4a}$, —$OR^{3a}$, —OC(O)$R^{3a}$, —OC(O)$NR^{3a}R^{4a}$, —$SR^{3a}$, —S(O)$R^{3a}$, —S(O)$_2R^{3a}$, —S(O)$_2NR^{3a}R^{4a}$, —NO$_2$, —$NR^{3a}R^{4a}$, —$NR^{3a}C(O)R^{4a}$, —$NR^{3a}C(O)OR^{4a}$, —$NR^{3a}S(O)_2R^{4a}$, —$NR^{3a}C(O)NR^{4a}R^{5a}$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^{3a}$, $R^{4a}$, and $R^{5a}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^{3a}$ and $R^{4a}$, $R^{4a}$ and $R^{5a}$ or $R^{3a}$ and $R^{5a}$ may, together with the atoms to which they are attached, form a substituted or unsubstituted 5-, 6-, or 7-membered ring;

L is selected from the group consisting of a bond, —O—, —S—, —S(O)—, —S(O)$_2$—, —$CR^6R^7$—, —$NR^8$—, —C(O)— and —$NR^8C(O)$—;

$R^6$ and $R^7$ are each independently selected from the group consisting of hydrogen, halogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, —CN, —$OR^9$, —$NR^{10}R^{11}$, —S(O)$R^9$, and —S(O)$_2R^9$;

$R^6$ and $R^7$ may, together with the carbon atom to which they are attached, form substituted or unsubstituted $C_{3-8}$ cycloalkyl or substituted or unsubstituted 3- to 10-membered heterocyclic ring;

$R^9$ is selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^{10}$ and $R^{11}$ are each independently selected from the group consisting of substituted or unsubstituted $C_{1-8}$ alkyl, substituted or unsubstituted 3- to 10-membered heterocyclyl, substituted or unsubstituted $C_{6-10}$ aryl, substituted or unsubstituted 5- to 10-membered heteroaryl, substituted or unsubstituted $C_{2-8}$ alkenyl, and substituted or unsubstituted $C_{2-8}$ alkynyl;

$R^{10}$ and $R^{11}$ of —$NR^{10}R^{11}$ may, together with the nitrogen, form a substituted or unsubstituted $C_{3-8}$ cycloalkyl or substituted or unsubstituted 3- to 10-membered heterocyclyl;

$R^8$ is selected from the group consisting of hydrogen, $C(O)R^{12}$, $S(O)_2R^{12}$, $CO_2R^{12}$, substituted or unsubstituted $C_{1-8}$ alkyl, substituted or unsubstituted 3- to 10-membered heterocyclyl, substituted or unsubstituted $C_{2-6}$ alkenyl, and substituted or unsubstituted $C_{2-6}$ alkynyl;

$R^{12}$ is selected from the group consisting of substituted or unsubstituted $C_{1-8}$ alkyl, substituted or unsubstituted $C_{2-6}$ alkenyl, substituted or unsubstituted $C_{2-6}$ alkynyl, substituted or unsubstituted 3- to 10-membered heterocyclyl, substituted or unsubstituted $C_{6-10}$ aryl, and substituted or unsubstituted 5- to 10-membered heteroaryl;

$Z^1$ is selected from the group consisting of substituted or unsubstituted $C_{6-10}$ aryl, substituted or unsubstituted 5- to 10-membered heteroaryl, substituted or unsubstituted 3- to 10-membered heterocyclyl, and —$NR^{13}R^{14}$;

$R^{13}$ and $R^{14}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, substituted or unsubstituted 5- to 10-membered heteroaryl, substituted or unsubstituted ($C_{1-4}$ alkyl)-($C_{6-10}$ aryl), and substituted or unsubstituted ($C_{1-4}$ alkyl)-(5- to 10-membered heteroaryl);

$R^{13}$ and $R^{14}$ may, together with the nitrogen, form a substituted or unsubstituted 4-, 5-, 6-, or 7-membered heterocyclyl;

$Y^4$ is selected from the group consisting of —N— and —N$^+$(O)$^-$—.

In some embodiments, the compounds of formula CC are excluded from formula (Ia):

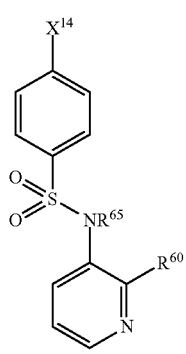

CC where $X^{14}$ is selected from the group consisting of —Cl, —NO$_2$, —OCH$_3$, —CH$_3$, —NHC(O)CH$_3$, and —CH$_2$CH$_2$-(phenyl);

$R^{65}$ is selected from the group consisting of hydrogen, substituted or unsubstituted $C_{1-4}$ alkyl, and substituted or unsubstituted —SO$_2$(phenyl); and $R^{60}$ is selected from the group consisting of —NR$^{61}$CH$_2$CH$_2$OR$^{62}$, —NR$^{61}$CH$_2$CH$_2$NR$^{63}$R$^{64}$, —NR$^{61}$CH$_2$CH$_2$SR$^{62}$,

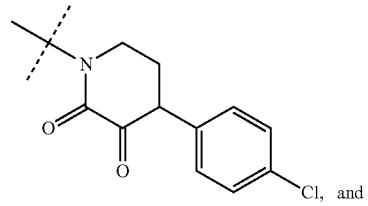

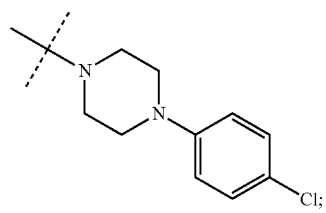

where $R^{61}$ is selected from the group consisting of hydrogen and substituted or unsubstituted phenyl;

$R^{62}$ is selected from the group consisting of substituted or unsubstituted phenyl, and substituted or unsubstituted $C_{1-4}$ alkyl; and $R^{63}$ and $R^{64}$ are each independently selected from the group consisting of hydrogen, substituted or unsubstituted $C_{1-8}$ alkyl, substituted or unsubstituted phenyl, substituted or unsubstituted —SO$_2$(phenyl), —C(O)CH$_3$, —C(O)C(O)OH, and —C(O)$_2$C(CH$_3$)$_3$.

In some embodiments, $Z^1$ is substituted or unsubstituted 5- to 10-membered heteroaryl.

In some embodiments, L is —C(O)—.

In some embodiments, $Y^1$ is —CR$^{2a}$—; $Y^2$ is —CR$^{2b}$—; $Y^3$ is —CR$^{2c}$—; and R$^{2a}$, R$^{2b}$, and R$^{2c}$ are each independently selected from the group consisting of hydrogen, halogen, substituted or unsubstituted $C_{1-8}$ alkyl.

In some embodiments, $R^{1a}$ is selected from the group consisting of hydrogen or substituted or unsubstituted $C_{1-8}$ alkyl.

In some embodiments, Ar$^1$ is substituted or unsubstituted $C_{6-10}$ aryl.

In some embodiments, $Y^4$ is —N—.

In some embodiments, $Z^1$ is substituted or unsubstituted 5- to 10-membered heteroaryl; L is —C(O)—; $Y^1$ is —CR$^{2a}$—; $Y^2$ is —CR$^{2b}$—; $Y^3$ is —CR$^{2c}$—, R$^{2a}$, R$^{2b}$, and R$^{2c}$ are each independently selected from the group consisting of hydrogen, halogen, substituted or unsubstituted $C_{1-8}$ alkyl; $R^{1a}$ is selected from the group consisting of hydrogen or substituted or unsubstituted $C_{1-8}$ alkyl; Ar$^1$ is substituted or unsubstituted $C_{6-10}$ aryl; and $Y^4$ is —N—.

The present disclosure provides methods of treating liver fibrosis in a patient comprising administering to the patient in need thereof an effective amount of a compound of Formula I:

Formula I

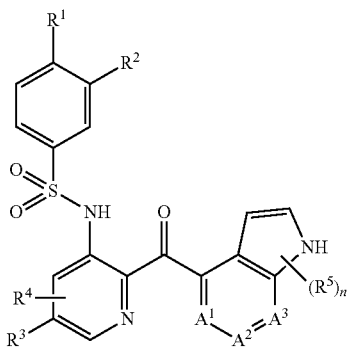

or a pharmaceutically acceptable salt thereof, wherein $R^1$ is halogen or $C_{1-6}$ alkyl;

$R^2$ is hydrogen, halogen, $C_{1-6}$ alkyl, $C_{1-6}$ alkoxy, $C_{1-6}$ haloalkyl, $C_{1-6}$ haloalkoxy, or —CN;

$R^3$ is hydrogen, halogen, or $C_{1-6}$ alkyl;

$R^4$ is hydrogen, halogen, or $C_{1-6}$ alkyl;

each $R^5$ is independently $C_{1-6}$ alkyl, —OH, or —NH$_2$;

n is 0, 1, 2, or 3; and each of $A^1$, $A^2$, and $A^3$ is —CH— or —N—, where at least one of $A^1$, $A^2$, or $A^3$ is —N—.

In some embodiments, $R^1$ is halogen or methyl; $R^2$ is halogen or $C_{1-6}$ haloalkyl; $R^3$ is halogen or $C_{1-6}$ alkyl; $R^4$ is hydrogen; n is 0; $A^2$ is —CH—; and $A^3$ is —N—.

In some embodiments, the compound is selected from the group consisting of:

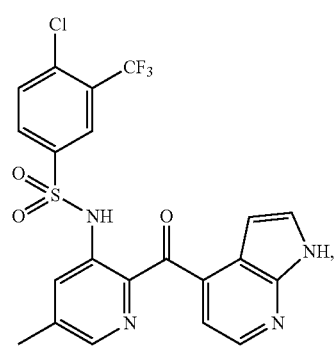

1

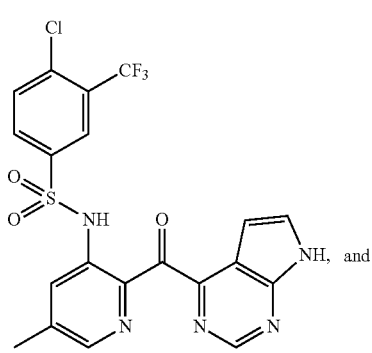

2

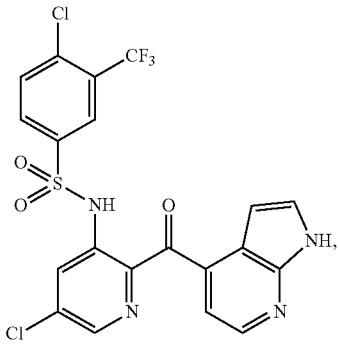

3 or a pharmaceutically acceptable salt thereof.

In some embodiments, the compound is

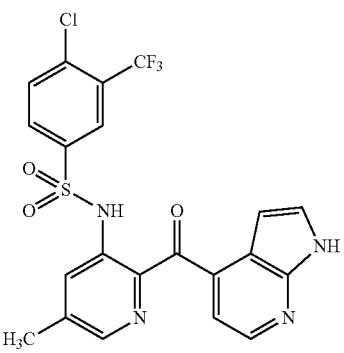 [SMILES: Cc1cnc(C(=O)c2ccnc3[nH]ccc23)c(NS(=O)(=O)c2ccc(Cl)c(C(F)(F)F)c2)c1]

1 or a pharmaceutically acceptable salt thereof.

In some embodiments, the liver fibrosis is associated with non-alcoholic steatohepatitis (NASH).

In some embodiments, the NASH is associated with type 2 diabetes mellitus (T2DM).

In some embodiments, the NASH is associated with metabolic syndrome (MS).

In some embodiments, the liver fibrosis is associated with non-alcoholic fatty liver disease (NAFLD).

In some embodiments, the NAFLD is associated with type 2 diabetes mellitus (T2DM).

In some embodiments, the NAFLD is associated with metabolic syndrome (MS).

In some embodiments, the liver fibrosis is associated with emerging cirrhosis. In some embodiments, the cirrhosis is associated with alcohol damage.

In some embodiments, the liver fibrosis comprises non-cirrhotic hepatic fibrosis.

In some embodiments, the liver fibrosis is associated with a hepatitis infection, including but not limited to hepatitis B, hepatitis C, and hepatitis D.

In some embodiments, the liver fibrosis is associated with one or more of emerging cirrhosis, primary biliary cholangitis, primary sclerosing cholangitis, biliary atresia, cholestatic liver disease, chronic liver disease, alcoholic liver disease, hypercholesteremia, and hyperlipidemia.

In some embodiments, the liver fibrosis is associated with primary biliary cirrhosis (PBC), biliary atresia or primary sclerosing cholangitis.

In some embodiments, the liver fibrosis is associated with primary biliary cholangitis, primary sclerosing cholangitis, or biliary atresia.

In some embodiments, the patient being treated is infected with a virus. In some embodiments, the virus is a hepatitis virus, including but not limited to HCV (hepatitis C virus), HBV and HDV. In some embodiments, the subject has diabetes. In some embodiments, the subject has type 2 diabetes. In some embodiments, the subject has type 1 diabetes. In some embodiments, the subject has metabolic syndrome (MS). In some embodiments, the subject has one or more of these diseases or disorders. In some embodiments, the subject is at risk of developing one or more of these diseases. In some embodiments, the subject has insulin resistance. In some embodiments, the subject has increased blood glucose concentrations, high blood pressure, elevated cholesterol levels, elevated triglyceride levels, or is obese. In some embodiments, the subject has polycystic ovary syndrome.

In some embodiments, the patient being treated is at risk of developing liver fibrosis or cirrhosis.

In some embodiments, the fibrosis comprises non-cirrhotic hepatic fibrosis.

In some embodiments, the liver fibrosis is advanced.

In some embodiments, the compound or a pharmaceutically acceptable salt thereof is administered orally.

In some embodiments, the compound or a pharmaceutically acceptable salt thereof is administered once per day or twice per day.

In some embodiments, the compound or a pharmaceutically acceptable salt thereof is administered once per day.

In some embodiments, the method further comprises administering to the patient one or more additional therapeutic compound.

In some embodiments, the one or more additional therapeutic compound is selected from one or more of a sodium glucose transporter-2 inhibitor, a glucagon-like peptide 1 agonist, a galectin-3 inhibitor, a transaminase stimulator, an IL-10 agonist, an insulin sensitizer, a PPAR gamma agonist, a thyroid hormone receptor beta agonist, a caspase inhibitor, a dipeptidyl peptidase IV inhibitor, a PPAR alpha agonist; a PPAR delta agonist, a PPAR agonist, farnesoid X receptor agonist, a lysyl oxidase homolog 2 inhibitor, a MEKK-5 protein kinase inhibitor, a methyl CpG binding protein 2 modulator, a transglutaminase inhibitor, a myelin basic protein stimulator, a chloride channel stimulator, a CCR3 chemokine antagonist, a CCR5 chemokine antagonist, an angiotensin II AT-1 receptor antagonist, a SREBP transcription factor 1 inhibitor, a PDGF receptor beta modulator, a FGF-21 ligand, an IL-17 antagonist, a rho associated protein kinase 2 inhibitor, an ileal sodium bile acid cotransporter inhibitor, a stearoyl CoA desaturase-1 inhibitor, a FGF1 receptor agonist, a klotho beta stimulator, a connective tissue growth factor ligand inhibitor, a lipoprotein lipase inhibitor; a SREBP transcription factor inhibitor, a FGF-19 ligand, a CD3 antagonist, a caveolin 1 inhibitor, an amylin receptor agonist; a calcitonin agonist, a NAD-dependent deacetylase sirtuin stimulator, a PDE 5 inhibitor, a NADPH oxidase 1 inhibitor, a NADPH oxidase 4 inhibitor, a NADPH oxidase inhibitor, an hepatocyte growth factor agonist, an integrin alpha-V/beta-6 antagonist, TGF beta antagonist, a NAD-dependent deacetylase sirtuin stimulator, a nicotinic acid receptor 1 agonist, a phenylalanine hydroxylase stimulator, a membrane copper amine oxidase inhibitor, a ribosomal protein S6 kinase-1 inhibitor, a high mobility group protein B1 inhibitor, a TLR-4 antagonist, a cathepsin B inhibitor, a hepatocyte growth factor ligand, an interferon gamma ligand, an ACE inhibitor, a HMG CoA reductase inhibitor, or a pharmaceutically acceptable salt thereof.

In some embodiments, the one or more additional therapeutic compound is selected from one or more of a farnesoid X receptor (FXR) agonist, a dual TGR5/FXR agonist, a PPAR alpha agonist, a PPAR-gamma agonist, a PPAR-delta agonist, or a pharmaceutically acceptable salt thereof.

In some embodiments, the one or more additional therapeutic compound is selected from one or more of dapagliflozin propanediol, dapagliflozin, liraglutide, GR-MD-02, semaglutide, cenicriviroc, F-351, peg-ilodecakin, ipragliflozin, ursodeoxycholic acid, colesevelam, pioglitazone, VK-2809, emricasan, linagliptin, elafibranor, DS-102, Px-102, Px-103, GS-4997, simtuzumab, DUR-928, mercaptamine, olesoxime, cobiprostone, bertilimumab, MDV-4463, irbesartan, GS-9674, BOT-191, MGL-3196, BMS-986171, PEG-FGF21, LJN-452, CF-102, KD-025, volixibat, volixibat potassium ethanolate hydrate, aramchol, tipelukast, NGM-313, FG-3019, CAT-2003, NGM-282, TRX-318, IONIS-DGAT2Rx, IMM-124-E, RG-125, norursodeoxycholic acid, KBP-042, leucine, metformin, sildenafil, A-4250, GKT-831, BB-3, saroglitazar, BG-00011, alipogene tiparvovec, MB-12066, betaine anhydrous, ARI-3037MO, HepaStem, PXS-4728A, CIGB-500, oltipraz, omega-3 carboxylic acids, dapagliflozin, remogliflozin etabonate, remogliflozin, LC-280126, JKB-121, DWP-10292, VBY-376, VBY-825, icosapent ethyl ester, Fuzheng Huayu capsule, interferon gamma, acetylsalicylic acid, hydrochlorothiazide, enalapril, atorvastatin, NC-101, TCM-606F, obeticholic acid, INT-767, GNF-5120, cryptochinone-D, fexaramine, caprylic triglyceride, evogliptin, GM-CT-01, high dose vitamin E (>400 iU/d) or a pharmaceutically acceptable salt thereof.

In some embodiments, the one or more additional therapeutic compound may be administered simultaneously with the compound of Formula (I), (Ia), compound 1, 2, or 3 or a pharmaceutically acceptable salt thereof, or be administered separately, including at different times and with different frequencies. The one or more additional therapeutic compound may be administered by any known route, such as orally, intravenously, intramuscularly, nasally, subcutaneously, intra-vaginally, intra-rectally, and the like; and the compound of Formula (I), (Ia), compound 1, 2, or 3 or a pharmaceutically acceptable salt thereof may also be administered by any conventional route. In some embodiments, the one or more additional therapeutic compound and the compound of Formula (I), (Ia), compound 1, 2, or 3 or a pharmaceutically acceptable salt thereof are administered orally.

When two or more medicines are used in combination, dosage of each medicine is commonly identical to the dosage of the medicine when used independently, but when a medicine interferes with metabolism of other medicines, the dosage of each medicine is properly adjusted. Each medicine may be administered simultaneously or separately in a time interval for example of less than 12 hours, 24 hours, 36 hours. A dosage form as described herein, such as a capsule, can be administered at appropriate intervals. For example, once per day, twice per day, three times per day, and the like. In particular, the dosage form is administered for example, once or twice per day. Even more particularly, the dosage form is administered once per day.

In some embodiments, the compound of Formula (I), (Ia), compound 1, 2, or 3 or a pharmaceutically acceptable salt thereof improves insulin sensitivity.

In some embodiments, the compound of Formula (I), (Ia), compound 1, 2, or 3 or a pharmaceutically acceptable salt thereof improves glucose tolerance.

In some embodiments, the compound of Formula (I), (Ia), compound 1, 2, or 3 or a pharmaceutically acceptable salt thereof lowers hepatic triglyceride accumulation.

In some embodiments, the compound of Formula (I), (Ia), compound 1, 2 or 3 or a pharmaceutically acceptable salt thereof lowers alanine aminotransferase (ALT) concentration.

In some embodiments, the compound of Formula (I), (Ia), compound 1, 2 or 3 or a pharmaceutically acceptable salt thereof lowers aspartate aminotransferase (AST) concentration.

In some embodiments, the compound of Formula (I), (Ia), compound 1, 2, or 3 or a pharmaceutically acceptable salt thereof lowers liver collagen content.

In some embodiments, the compound of Formula (I), (Ia), compound 1, 2, or 3 or a pharmaceutically acceptable salt thereof lowers hepatic macrophages content.

In some embodiments, the compound of Formula (I), (Ia), compound 1, 2, or 3 or a pharmaceutically acceptable salt thereof lowers adipose tissue macrophages content.

In some embodiments, the compound of Formula (I), (Ia), compound 1, 2, or 3 or a pharmaceutically acceptable salt thereof lowers omental adipose tissue content.

In some embodiments, the compound of Formula (I), (Ia), compound 1, 2, or 3 or a pharmaceutically acceptable salt thereof lowers liver cholesterol levels.

In some embodiments, the compound of Formula (I), (Ia), compound 1, 2, or 3 or a pharmaceutically acceptable salt thereof lowers bilirubin levels.

In some embodiments, the compound of Formula (I), (Ia), compound 1, 2, or 3 or a pharmaceutically acceptable salt thereof reduces liver fibrosis. Compounds that Modulate CCR2 Activity The present disclosure provides compounds that modulate CCR2 activity. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

Without intending to be bound by any particular theory, it is believed that the compounds provided herein interfere with the interaction between a chemokine receptor and one or more cognate ligands. In particular, it is believed that the compounds interfere with the interaction between CCR2 and a CCR2 ligand, such as MCP-1. Compounds contemplated by the disclosure include, but are not limited to, the exemplary compounds provided herein and salts thereof.

The compounds of the disclosure are thought to interfere with inappropriate T-cell trafficking by specifically modulating or inhibiting a chemokine receptor function. Compounds contemplated by the disclosure include, but are not limited to the exemplary compounds provided herein and pharmaceutically acceptable salts thereof and the compounds provided in U.S. Pat. No. 8,519,135, US 2006/0173019, U.S. Pat. Nos. 7,622,583, 7,884,110 and 8,093,247, which are hereby incorporated by reference.

In some embodiments, the compounds of the disclosure do not inhibit CCR5.

In some embodiments, the compounds of the disclosure are selective inhibitors of CCR2 over CCR5.

In some embodiments, the compounds of the disclosure have over 10 fold selectivity for CCR2 inhibition over CCR5 inhibition.

In some embodiments, the compounds of the disclosure have over 100 fold selectivity for CCR2 inhibition over CCR5 inhibition.

In some embodiments, the compounds of the disclosure are selective inhibitors of CCR2.
Compositions Pharmaceutically acceptable compositions can be administered to humans and other animals orally, rectally, parenterally, intracisternally, intravaginally, intraperitoneally, topically (as by powders, ointments, or drops), bucally, as an oral or nasal spray, or the like.

Liquid dosage forms for oral administration include, but are not limited to, pharmaceutically acceptable emulsions, microemulsions, solutions, suspensions, syrups and elixirs. In addition to the active compound(s), a liquid dosage form may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be incorporated in an injectable product. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The compounds of the present disclosure or a pharmaceutically acceptable salt thereof may be formulated using nanotechnology. Nanoparticles are attractive for medical purposes based on their unique features, such as their surface to mass ratio being larger than that of other particles, their quantum properties, and their ability to adsorb and carry other compounds. Nanoparticles may have dimensions below 0.1 µm or 100 nm. Alternatively, a pharmaceutical composition may comprise relatively large (size>100 nm) nanoparticles, as needed for loading a sufficient amount of drug onto the particles. In addition, for drug delivery, not only engineered particles may be used as carrier, but also the drug itself may be formulated at a nanoscale, and then function as its own carrier. The composition of the engineered nanoparticles may vary. Source materials may be of biological origin like phospholipids, lipids, lactic acid, dextran, chitosan, or have more chemical characteristics like various polymers, carbon, silica, and metals. Especially in the area of engineered nanoparticles of polymer origin there is a vast area of possibilities for the chemical composition. See, for example, Martins et al., Nanoparticle Drug Delivery Systems: Recent Patents and Applications in Nanomedicine, Recent Patents on Nanomedicine, 2013, 3(2), pp. 1-14.

The compounds of the present disclosure or a pharmaceutically acceptable salt thereof may also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, for example tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this disclosure. Additionally, the disclosure contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds and compositions of the present disclosure may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non toxic pharmaceutically acceptable carriers, adjuvants and vehicles appropriate for each rouse of administration. The present disclosure also contemplates administration of the compounds and compositions of the present disclosure in a depot formulation.

In the treatment or prevention of conditions which require chemokine receptor modulation an appropriate dosage level of the compound of Formula (I), (Ia), compound 1, 2, or 3 or a pharmaceutically acceptable salt thereof will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 80.0, 90.0, 100.0, 110.0, 120.0, 130.0, 140.0, 150.0, 160.0, 170.0, 180.0, 190.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

The compounds and compositions of the present disclosure can be combined with other compounds and compositions having related utilities to prevent and treat liver fibrosis, NASH, NAFLD, emerging cirrhosis and/or non-cirrhotic hepatic fibrosis. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

The weight ratio of the compound of the present disclosure to another active ingredient may be varied and will depend upon the effective dose of each ingredient. Generally, an effective dose of each will be used. Thus, for example, when a compound of the present disclosure is combined with a second therapeutic compound the weight ratio of the compound of the present disclosure to the second therapeutic compound will generally range from about 1000:1 to about 1:1000, preferably about 200:1 to about 1:200.

In yet another aspect, the present disclosure provides methods of treating or preventing liver fibrosis, NASH, NAFLD, emerging cirrhosis and/or non-cirrhotic hepatic fibrosis by administering to a subject having such a condition or disease a therapeutically effective amount of any compound of the present disclosure. Compounds for use in the present methods include those compounds according to Formula (I), (Ia), compound 1, 2 or 3 or a pharmaceutically acceptable salt thereof, those provided as embodiments, those provided with specific structures herein and the compounds provided in U.S. Pat. No. 8,519,135, US 2006/0173019, U.S. Pat. Nos. 7,622,583, 7,884,110 and 8,093,247 which are hereby incorporated by reference. The compounds can be useful to treat a subject in need of treatment. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "therapeutically effective amount" means the amount of the subject compound that will elicit the biological or medical response of a cell, tissue, system, or animal, such as a human, that is being sought by the researcher, veterinarian, medical doctor or other treatment provider.

In one embodiment, the present disclosure provides methods of treating or preventing liver fibrosis, NASH, NAFLD, emerging cirrhosis and/or non-cirrhotic hepatic fibrosis involving administering to a subject an effective amount of the compound or composition of the disclosure, where the administering is oral, parenteral, rectal, transdermal, sublingual, nasal or topical.

CCR2 Modulators

The following examples are offered to illustrate, but not to limit, the present disclosure.

Certain molecules disclosed in this patent can exist in different enantiomeric and diastereomeric forms and all such variants of these compounds are within the scope of the disclosure.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present disclosure.

Although specific embodiments of the present disclosure are herein illustrated and described in detail, the disclosure is not limited thereto. The above detailed descriptions are provided as exemplary of the present disclosure and should not be construed as constituting any limitation of the disclosure. Modifications will be obvious to those skilled in the art, and all modifications that do not depart from the spirit of the disclosure are intended to be included with the scope of the appended claims.

EXAMPLES

Compound 1 is:

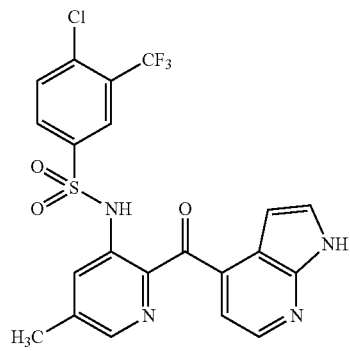

CVC is cenicriviroc.

Example 1

High Fat Diet (HFD) Induced NASH Model

Male wild-type (WT) mice C57Bl/6 were obtained from Jackson Laboratory and fed either with high-fat diet (D12492, 60 Cal % fat, Research Diets, New Brunswick, N.J.) with 30% fructose in the drink water or a lean control diet (D12450B, 10 Cal % fat, Research Diets) at 6-8 week of age and maintained on the respective diet for the duration of the study (16-32 weeks). Compound 1 was formulated as a solution in 1% hydroxypropyl methylcellulose (Sigma-Aldrich, St. Louis, USA). Mice were dosed subcutaneously once per day with 30 mg/kg of Compound 1 or vehicle for 8 weeks. As illustrated by FIG. 1, treatment with compound 1 did not change the body weight compared to vehicle. As shown in FIG. 2, Compound 1 reduced serum ALT and AST levels. Sirius red-staining was used to evaluate the severity of liver fibrosis. FIG. 3 shows representative images of Sirius red-stained liver sections of animals treated with Compound 1 or vehicle. FIG. 4 shows that treatment with compound 1 reduced the percentage of Sirius staining and, therefore, liver fibrosis compared to vehicle.

Example 2

Methionine-Choline Deficient (MCD) Induced NASH Model

Male wild-type (WT) mice C57Bl/6 were obtained from Jackson Laboratory and fed either with MCD diet (MP Biomedicals, #960439) or a lean control diet at 8 week of age for 8 weeks. Compound 1 was formulated as a solution in 1% hydroxypropyl methylcellulose (Sigma-Aldrich, St. Louis, USA). Mice were dosed subcutaneously once per day with 30 mg/kg Compound 1 or vehicle for 8 weeks. Compound 1 was administered subcutaneously to maintain high systemic levels. The CVC compound (cenicriviroc) was formulated as a solution in 1% hydroxypropyl methylcellulose, and tested at 30 mg/kg orally. For both compound 1 and CVC, trough drug level was over $IC_{50}$. FIG. 5 shows that compound 1 significantly reduces serum ALT levels whereas CVC does not. FIG. 6 shows that compound 1 reduces Sirius red-positive staining and, therefore, liver fibrosis, whereas CVC does not.

Example 3

Histopathological Analysis

Formalin-fixed, paraffin-embedded liver sections were stained separately with hematoxylin & eosin (H&E) and for Sirius red Picrosirius red (#365548, Sigma) and evaluated for severity of liver fibrosis. All pathologic evaluations were made by a pathologist on a random and blinded basis. Collagen surface density was quantified using Image J (NIH). Two Sirius red-stained slides per animal were taken at different depth, with 18 images taken randomly per slide for a total of 36 images per animal for collagen quantification.

Example 4

Serum and Tissue Analysis

Liver enzymes were assayed by Antech GLP (Morrisville, N.C.). Insulin was measured with Ultrasensitive. Mouse Insulin ELISA kit (Crystal Chem Inc: #90080); Blood glucose and insulin levels were determined after an overnight fast (14-16 h). Insulin sensitivity was determined by the homeostatic model assessment of insulin resistance (HOMA-IR). Lipids were measured in the serum and liver with a Triglyceride Colorimetric Assay kit (Cayman Chemical Company: #10010303), a Free Fatty Acid Quantification kit, (Abcam, ab65341) and Cholesterol Quantification kit (Abcam, ab65359).

Example 5

CCR5 Migration Assay

A conventional migration assay was used to determine the efficacy of potential receptor antagonists in blocking migration mediated through MIP1b. This assay was routinely performed using the ChemoTX® (Neuroprobe) microchamber system with a 5-mum pore-sized polycarbonate membrane. CCR5 expressing cells (IL-2 Lymphocytes or L1.2CCR5 cells) were harvested by centrifugation of cell suspension at 1000 RPM on a GS-6R Beckman centrifuge. The cell pellet was resuspended in chemotaxis buffer (HBSS with 0.1 percent BSA) at $5\times10^6$ cells/mL. Test compounds at desired concentrations were prepared from 10 mM stock solutions by serial dilutions in chemotaxis buffer. An equal volume of cells and compounds were mixed and incubated at room temperature for 15 minutes. Afterwards, 20 μl of the mixture was transferred onto the porous membrane of a migration microchamber, with 29 μl of MIP1b ligand (0.1 nM MIP1b protein) placed at the lower chamber. Following incubation at 37 degrees centigrade (90-minute), the assay was terminated by removing the cell drops from atop the filter. To quantify cells migrated across the membrane, 5 mul_ of 7× CyQUANT® (ThermoFisher) solution was added to each well in the lower chamber, and the fluorescence signal measured on a Spectrafluor Plus fluorescence plate reader (TECAN, Durham, N.C.). The degree of inhibition was determined by comparing migration signals between compound-treated and untreated cells. $IC_{50}$ calculation was further performed by non-linear squares regression analysis using Graphpad Prism (Graphpad Software, San Diego, Calif.).

As illustrated in Table 1, compounds 1, 2, and 3 do not inhibit CCR5 whereas CVC is a potent CCR5 inhibitor.

TABLE 1

| | CCR5 $IC_{50}$ |
|---|---|
| Compound 1 | >5 μM |
| Compound 2 | >20 μM |
| Compound 3 | >20 μM |
| CVC (cenicriviroc) | 1 nM |

The invention claimed is:
1. A method of treating liver fibrosis in a patient comprising administering to the patient with liver fibrosis an effective amount of a compound of Formula I:

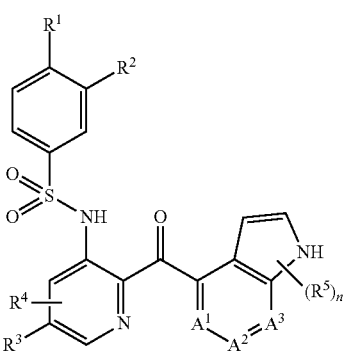

Formula I or a pharmaceutically acceptable salt thereof, wherein
$R^1$ is halogen or $C_{1-6}$ alkyl;
$R^2$ is hydrogen, halogen, $C_{1-6}$ alkyl, $C_{1-6}$ alkoxy, $C_{1-6}$ haloalkyl, $C_{1-6}$ haloalkoxy, or —CN;
$R^3$ is hydrogen, halogen, or $C_{1-6}$ alkyl;
$R^4$ is hydrogen, halogen, or $C_{1-6}$ alkyl;

each $R^5$ is independently $C_{1-6}$ alkyl, OH, or —$NH_2$;

n is 0, 1, 2, or 3; and each of $A^1$, $A^2$, and $A^3$ is —CH— or —N—, where at least one of $A^1$, $A^2$, or $A^3$ is —N—.

2. The method of claim 1 wherein $R^1$ is halogen or methyl;

$R^2$ is halogen or $C_{1-6}$ haloalkyl;

$R^3$ is halogen or $C_{1-6}$ alkyl;

$R^4$ is hydrogen;

n is 0;

$A^2$ is —CH—; and $A^3$ is —N—.

3. The method of claim 1, wherein the compound is selected from the group consisting of:

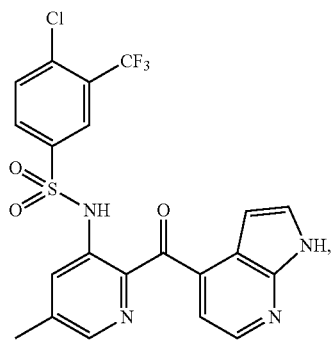

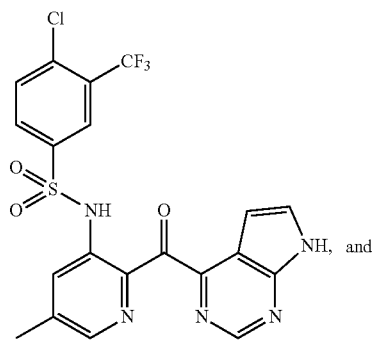

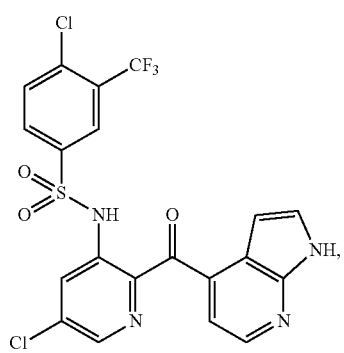

or a pharmaceutically acceptable salt thereof.

4. The method of claim 1, wherein the compound is

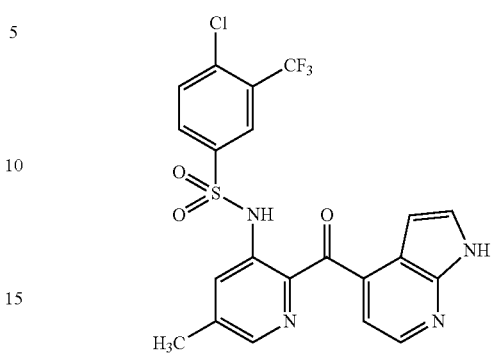

or a pharmaceutically acceptable salt thereof.

5. The method of claim 1, wherein the liver fibrosis is associated with non-alcoholic steatohepatitis (NASH).

6. The method of claim 1, wherein the liver fibrosis is associated with non-alcoholic fatty liver disease (NAFLD).

7. The method of claim 1, wherein the liver fibrosis is associated with one or more of emerging cirrhosis, primary biliary cholangitis, primary sclerosing cholangitis, biliary atresia, cholestatic liver disease, chronic liver disease, hepatitis C infection, alcoholic liver disease, hypercholesteremia, and hyperlipidemia.

8. The method of claim 1, wherein the liver fibrosis is non-cirrhotic hepatic fibrosis.

9. The method of claim 1, wherein the NASH is associated with type 2 diabetes mellitus (T2DM).

10. The method of claim 1, wherein the NASH is associated with metabolic syndrome (MS).

11. The method of claim 1, further comprising administering to the patient one or more additional therapeutic compound.

12. The method of claim 11 wherein the one or more additional therapeutic compound is selected from one or more of a sodium glucose transporter-2 inhibitor, a glucagon-like peptide 1 agonist, a galectin-3 inhibitor, a transaminase stimulator, an IL-10 agonist, an Insulin sensitizer, a PPAR gamma agonist, a thyroid hormone receptor beta agonist, a caspase inhibitor, a dipeptidyl peptidase IV inhibitor, a PPAR alpha agonist; a PPAR delta agonist, a PPAR agonist, farnesoid X receptor agonist, a lysyl oxidase homolog 2 inhibitor, a MEKK-5 protein kinase inhibitor, a methyl CpG binding protein 2 modulator, a transglutaminase inhibitor, a myelin basic protein stimulator, a chloride channel stimulator, a CCR3 chemokine antagonist, a CCR5 chemokine antagonist, an angiotensin II AT-1 receptor antagonist, a SREBP transcription factor 1 inhibitor, a PDGF receptor beta modulator, a FGF-21 ligand, an IL-17 antagonist, a rho associated protein kinase 2 inhibitor, an ileal sodium bile acid cotransporter inhibitor, a stearoyl CoA desaturase-1 inhibitor, a FGF1 receptor agonist, a klotho beta stimulator, a connective tissue growth factor ligand inhibitor, a lipoprotein lipase inhibitor; a SREBP transcription factor inhibitor, a FGF-19 ligand, a CD3 antagonist, a caveolin 1 inhibitor, an amylin receptor agonist; a calcitonin agonist, a NAD-dependent deacetylase sirtuin stimulator, a PDE 5 inhibitor, a NADPH oxidase 1 inhibitor, a NADPH oxidase 4 inhibitor, a NADPH oxidase inhibitor, an hepatocyte growth factor agonist, an integrin alpha-V/beta-6 antagonist, TGF beta antagonist, a NAD-dependent deacetylase sirtuin stimulator, a nicotinic acid receptor 1 agonist, a phenylalanine hydroxylase stimulator, a membrane copper amine oxidase inhibitor, a ribosomal protein S6 kinase-1 inhibitor, a high mobility group protein B1 inhibitor, a TLR-4 antagonist, a cathepsin B inhibitor, a hepatocyte growth factor ligand, an interferon gamma ligand, an ACE inhibitor, a HMG CoA reductase inhibitor, or a pharmaceutically acceptable salt thereof.

13. The method of claim 12 wherein the one or more additional therapeutic compound is selected from one or more of a farnesoid X receptor (FXR) agonist, a dual TGR5/FXR agonist, a PPAR alpha agonist, a PPAR-gamma agonist, a PPAR-delta agonist, or a pharmaceutically acceptable salt thereof.

14. The method of claim 12 wherein the one or more additional therapeutic compound is selected from one or more of dapagliflozin propanediol, dapagliflozin, liraglutide, GR-MD-02, semaglutide, cenicriviroc, F-351, peg-ilodecakin, ipragliflozin, ursodeoxycholic acid, colesevelam, pioglitazone, VK-2809, emricasan, linagliptin, elafibranor, DS-102, Px-102, Px-103, GS-4997, simtuzumab, DUR-928, mercaptamine, olesoxime, cobiprostone, bertilimumab, MDV-4463, irbesartan, GS-9674, BOT-191, MGL-3196, BMS-986171, PEG-FGF21, LJN-452, CF-102, KD-025, volixibat, volixibat potassium ethanolate hydrate, aramchol, tipelukast, NGM-313, FG-3019, CAT-2003, NGM-282, TRX-318, IONIS-DGAT2Rx, IMM-124-E, RG-125, norursodeoxycholic acid, KBP-042, leucine, metformin, sildenafil, A-4250, GKT-831, BB-3, saroglitazar, BG-00011, alipogene tiparvovec, MB-12066, Betaine anhydrous, ARI-3037MO, HepaStem, PXS-4728A, CIGB-500, oltipraz, omega-3 carboxylic acids, dapagliflozin, remogliflozin etabonate, remogliflozin, LC-280126, JKB-121, DWP-10292, VBY-376, VBY-825, icosapent ethyl ester, Fuzheng Huayu capsule, interferon gamma, acetylsalicylic acid, hydrochlorothiazide, enalapril, atorvastatin, NC-101, TCM-606F, obeticholic acid, INT-767, GNF-5120, cryptochinone-D, fexaramine, caprylic triglyceride, evogliptin, GM-CT-01, high dose vitamin E (>400 iU/d) or a pharmaceutically acceptable salt thereof.

15. The method of claim 1, further comprising improving one or more of insulin sensitivity and glucose tolerance.

16. The method of claim 1, further comprising lowering one or more of hepatic triglyceride accumulation, alanine aminotransferase (ALT) concentration, aspartate am inotransferase (AST) concentration, liver collagen content, hepatic macrophages content, adipose tissue macrophages content, omental adipose tissue content, liver cholesterol levels, and bilirubin levels.

17. The method of any claim 1, further comprising reducing liver fibrosis.

18. A method of treating liver fibrosis in a patient comprising administering to the patient in need thereof an effective amount of a compound of Formula I:

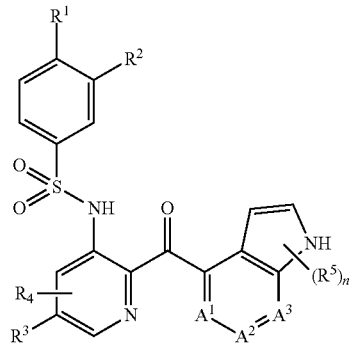

Formula I or a pharmaceutically acceptable salt thereof, wherein
$R^1$ is halogen or $C_{1-6}$ alkyl;
$R^2$ is hydrogen, halogen, $C_{1-6}$ alkyl, $C_{1-6}$ alkoxy, $C_{1-6}$ haloalkyl, $C_{1-6}$ haloalkoxy, or —CN;
$R^3$ is hydrogen, halogen, or $C_{1-6}$ alkyl;
$R^4$ is hydrogen, halogen, or $C_{1-6}$ alkyl;
each $R^5$ is independently $C_{1-6}$ alkyl, —OH, or —NH$_2$;
n is 0, 1, 2, or 3; and
each of $A^1$, $A^2$, and $A^3$ is —CH— or —N—, where at least one of $A^1$, $A^2$, or $A^3$ is —N—, wherein the liver fibrosis is associated with non-alcoholic steatohepatitis (NASH).

19. The method of claim 18, wherein the compound is selected from the group consisting of:

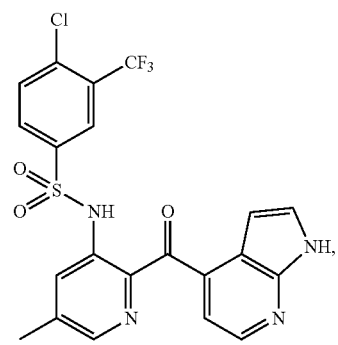

1

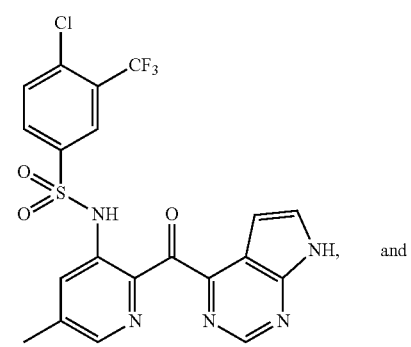

2 and

-continued

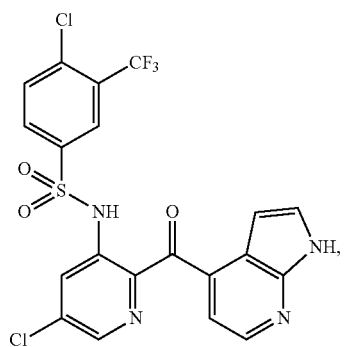

or a pharmaceutically acceptable salt thereof.

20. A method of treating liver fibrosis in a patient comprising administering to the patient in need thereof one or more additional therapeutic compound and an effective amount of a compound of Formula I:

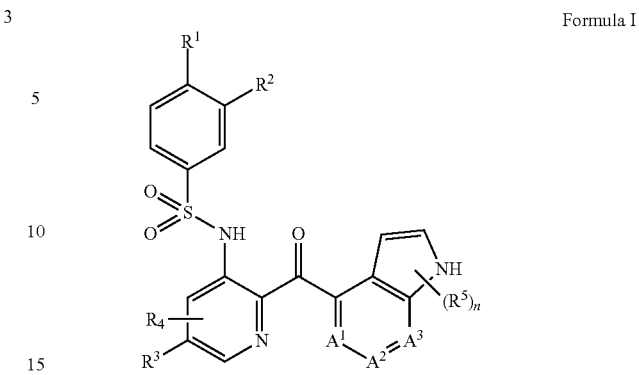

or a pharmaceutically acceptable salt thereof, wherein
$R^1$ is halogen or $C_{1-6}$ alkyl;
$R^2$ is hydrogen, halogen, $C_{1-6}$ alkyl, $C_{1-6}$ alkoxy, $C_{1-6}$ haloalkyl, $C_{1-6}$ haloalkoxy, or —CN;
$R^3$ is hydrogen, halogen, or $C_{1-6}$ alkyl;
$R^4$ is hydrogen, halogen, or $C_{1-6}$ alkyl;
each $R^5$ is independently $C_{1-6}$ alkyl, —OH, or —NH$_2$;
n is 0, 1, 2, or 3; and
each of $A^1$, $A^2$, and $A^3$ is —CH— or —N—, where at least one of $A^1$, $A^2$, or $A^3$ is —N—.

* * * * *

UNITED STATES PATENT AND TRADEMARK OFFICE
CERTIFICATE OF CORRECTION

PATENT NO. : 10,682,344 B2
APPLICATION NO. : 15/612124
DATED : June 16, 2020
INVENTOR(S) : Zhenhua Miao et al.

Page 1 of 1

It is certified that error appears in the above-identified patent and that said Letters Patent is hereby corrected as shown below:

In the Claims

Claim 9, Column 24, Line 34, delete "claim 1" and insert in place thereof --claim 5--
Claim 10, Column 24, Line 36, delete "claim 1" and insert in place thereof --claim 5--
Claim 16, Column 25, Lines 57 and 58, delete "am ino-transferase" and insert in place thereof --amino-transferase--

Signed and Sealed this
Twenty-eighth Day of July, 2020

Andrei Iancu
*Director of the United States Patent and Trademark Office*